(12) United States Patent
Inaki et al.

(10) Patent No.: US 8,673,803 B2
(45) Date of Patent: Mar. 18, 2014

(54) ALKALINE-EARTH METAL COMPOUND-CONTAINING ZEOLITE CATALYST, METHOD FOR PREPARING SAME, METHOD FOR REGENERATING SAME, AND METHOD FOR PRODUCING LOWER HYDROCARBONS

(71) Applicants: Chizu Inaki, Ishioka (JP); Hirofumi Ito, Chigasaki (JP); Kazunori Honda, Mito (JP); Koji Oyama, Yokohama (JP); Atsushi Okita, Mito (JP)

(72) Inventors: Chizu Inaki, Ishioka (JP); Hirofumi Ito, Chigasaki (JP); Kazunori Honda, Mito (JP); Koji Oyama, Yokohama (JP); Atsushi Okita, Mito (JP)

(73) Assignee: JGC Corporation, Tokyo (JP)

( * ) Notice: Subject to any disclaimer, the term of this patent is extended or adjusted under 35 U.S.C. 154(b) by 0 days.

(21) Appl. No.: 13/654,787

(22) Filed: Oct. 18, 2012

(65) Prior Publication Data

US 2013/0045861 A1 Feb. 21, 2013

Related U.S. Application Data

(62) Division of application No. 12/377,036, filed as application No. PCT/JP2007/066766 on Aug. 29, 2007, now abandoned.

(30) Foreign Application Priority Data

Aug. 30, 2006 (JP) ................................. 2006-234518
Sep. 27, 2006 (JP) ................................. 2006-262554
Sep. 28, 2006 (JP) ................................. 2006-266044

(51) Int. Cl.
*B01J 29/06* (2006.01)

(52) U.S. Cl.
USPC .................. 502/60; 502/63; 502/64; 502/68; 502/71; 502/77; 502/85

(58) Field of Classification Search
USPC .................. 502/60, 63, 64, 68, 71, 73, 77, 85
See application file for complete search history.

(56) References Cited

U.S. PATENT DOCUMENTS

| | | | |
|---|---|---|---|
| 4,326,994 A * | 4/1982 | Haag et al. ...................... 502/77 |
| 4,375,458 A | 3/1983 | Dwyer et al. | |
| 4,393,265 A | 7/1983 | Bonifaz | |
| 4,429,176 A | 1/1984 | Chester et al. | |
| 4,456,780 A | 6/1984 | Young | |
| 4,461,845 A | 7/1984 | Dessau et al. | |
| 4,544,793 A | 10/1985 | Okado et al. | |
| 4,559,314 A | 12/1985 | Shihabi | |
| 4,579,993 A | 4/1986 | Bowes et al. | |
| 4,663,492 A | 5/1987 | Chester et al. | |
| 4,748,747 A | 6/1988 | Schwar et al. | |
| 4,784,747 A | 11/1988 | Shihabi | |
| 5,506,182 A | 4/1996 | Yamagishi et al. | |
| 6,048,816 A * | 4/2000 | Brown et al. .................... 502/77 |
| 6,211,104 B1 | 4/2001 | Shi et al. | |
| 2005/0085375 A1 | 4/2005 | Bach et al. | |
| 2007/0032379 A1 | 2/2007 | Ito et al. | |

FOREIGN PATENT DOCUMENTS

| | | |
|---|---|---|
| EP | 0134333 | 3/1985 |
| EP | 0163429 | 12/1985 |
| EP | 0229952 | 7/1987 |
| JP | 58043928 | 3/1983 |
| JP | 59136138 | 8/1984 |
| JP | 60126233 | 7/1985 |
| JP | 60257838 | 12/1985 |
| JP | 62158224 | 7/1987 |
| JP | 363430 B2 | 10/1991 |
| JP | 2908959 B2 | 6/1999 |
| JP | 11192431 | 7/1999 |
| JP | 2005-138000 | 6/2005 |
| WO | WO-2005044760 | 5/2005 |
| WO | WO-2006/041253 A1 | 4/2006 |

OTHER PUBLICATIONS

Chang et al., "Insertion of Aluminium Into High-silica-content Zeolite Frameworks Part 3—Hydrothermal Transfer of Aluminium from $Al_2O_3$ into [Al]ZSM-5 and [B]ZSM-5", *Journal of the Chemical Society Faraday Transaction 1*, 1985, pp. 2215-2224, 81.

Shihabi et al., "Aluminum Insertion into High-Silica Zeolite Frameworks II, Binder Activation of High-Silica ZSM-5", *Journal of Catalysis 93*, 1985, pp. 471-474.

Zhu Hongfa, "Preparation for carrier of catalyst and application", *Petroleum Industry Publishing Company*, May 2002.

Chinese Office Action mailed May 19, 2011 for the corresponding Chinese Patent Application No. 200780030378.4.

GCC Office Action mailed Oct. 28, 2011 for the corresponding GCC Patent Application No. GCC/P/2007/8977.

Office Action mailed Sep. 4, 2012, for the corresponding Japanese Patent Application No. 2006-266044.

* cited by examiner

*Primary Examiner* — Elizabeth Wood
(74) *Attorney, Agent, or Firm* — Leason Ellis LLP

(57) ABSTRACT

An alkaline-earth metal compound-containing zeolite catalyst composed of a composite material comprising at least a first component, a second component, and a third component. The first component is composed of at least one of zeolites selected from a group consisting of proton-type zeolites and ammonium type zeolites. The second component is composed of at least one of alkaline-earth metal compounds. The third component is composed of at least one selected from a group consisting of aluminum oxides, aluminum hydroxides, silicon oxides, silicon hydroxides, and clay minerals. The first component has a molar ratio of Si/Al of 10 or more and 300 or less. Content of the second component relative to the first component is 0.3 mass % or more and less than 10 mass % as alkaline-earth metal. Content of the third component relative to the first component is 15 mass % or more and 200 mass % or less.

4 Claims, 1 Drawing Sheet

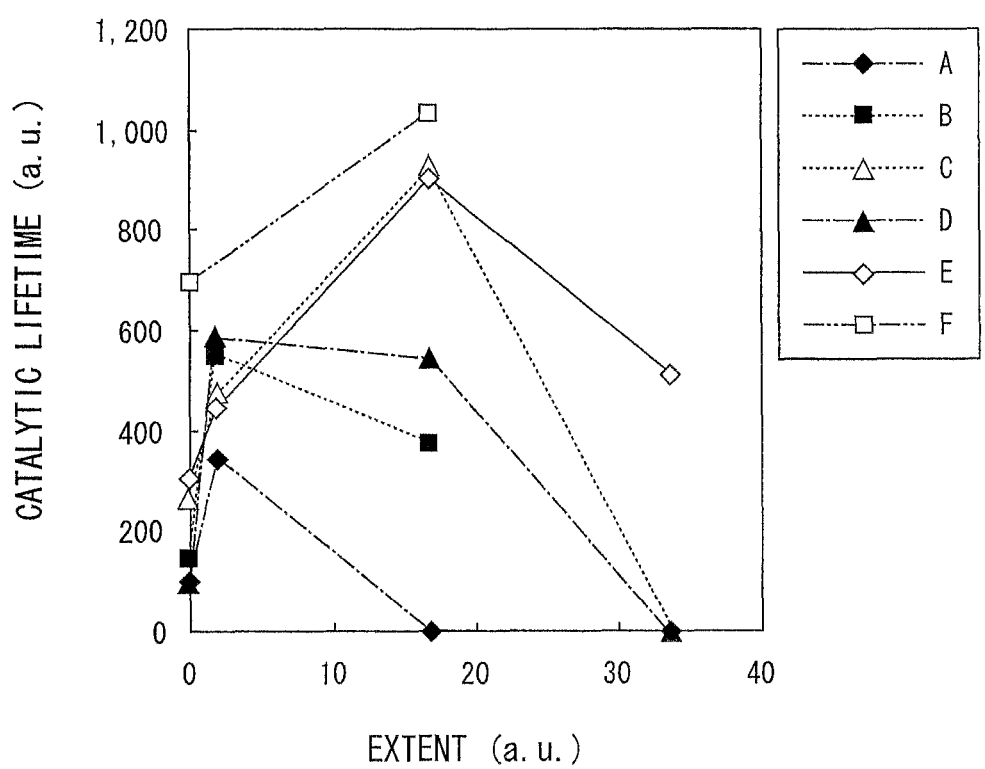

ALKALINE-EARTH METAL COMPOUND-CONTAINING ZEOLITE CATALYST, METHOD FOR PREPARING SAME, METHOD FOR REGENERATING SAME, AND METHOD FOR PRODUCING LOWER HYDROCARBONS

CROSS REFERENCE TO PRIOR APPLICATIONS

This application is a Divisional of U.S. patent application Ser. No. 12/377,036, filed Feb. 10, 2009 and now abandoned, which is a U.S. National Phase Application under 35 USC §371 of International Patent Application No. PCT/JP2007/066766, filed Aug. 29, 2007, and claims the priority of Japanese Patent Application Nos. 2006-234518, filed Aug. 30, 2006; 2006-262554, filed Sep. 27, 2006; and 2006-266044, filed Sep. 28, 2006, the contents of all of which are incorporated herein by reference. The International Application was published in Japanese on Mar. 6, 2008 as International Publication No. WO/2008/026638 under PCT Article 21 (2).

FIELD OF THE INVENTION

The present invention relates to an alkaline-earth metal compound-containing zeolite catalyst (zeolite-based catalyst that contains alkaline-earth metal compound) which is used in the synthetic process of lower hydrocarbons by dehydration condensation reaction from dimethyl ether and/or methanol, and also relates to a method for preparing the zeolite catalyst. Specifically, the present invention relates to an alkaline-earth metal compound-containing zeolite catalyst in which elimination of tetrahedral aluminum from zeolite framework is not likely to occur and exhibits slow formation rate of carbonaceous deposits during reaction, and relates to a method for producing the zeolite catalyst. The present invention also relates to a method for producing a lower hydrocarbons utilizing the alkaline-earth metal compound-containing zeolite catalyst. The present invention also relates to a method for regenerating the alkaline-earth metal compound-containing zeolite catalyst that is used in the synthetic process of lower hydrocarbons by dehydration condensation reaction from dimethyl ether and/or methanol.

BACKGROUND OF THE INVENTION

Zeolite catalysts are used in various processes such as DTO reaction/MTO reaction for synthesizing lower hydrocarbons from dimethyl ether (hereafter referred to as DME) and/or methanol, MTG reaction for synthesizing gasoline from methanol, fluid catalytic cracking (FCC) or the like.

In these processes, deactivation of zeolite catalysts may occur. For example, the following is the main reason for deactivating zeolite catalysts. Where the zeolite catalyst is exposed to the reaction atmosphere containing steam, elimination of aluminum from the zeolite framework (dealumination) may occur. In addition, carbonaceous deposits are formed on the zeolite catalysts during the reaction.

Reduction of catalytic activity caused by the formation of carbonaceous deposits on the catalyst may be solved by providing a flow containing oxygen to the catalyst and burning the carbonaceous deposits on the catalyst. On the other hand, as a countermeasure for reduction of catalytic activity caused by the elimination of aluminum from the zeolite framework, a method is proposed for inserting aluminum into the framework by treating the dealuminated zeolite in particular conditions.

As methods for regenerating a dealuminated zeolite, a method for regenerating the zeolite using aluminum chloride and acid (for example, Patent Reference 1: Japanese Unexamined Patent Application, First Publication No. S59-136138), and a method for regenerating the zeolite using steam and ammonia are disclosed (for example, Patent Reference 2: Japanese Unexamined Patent Application, First Publication No. S60-257838).

In addition, a method for inserting aluminum into a high-silica zeolite by compounding a high-silica zeolite with alumina (aluminum oxide) and treating the compounded material with steam is known (for example, Patent Reference 3: Japanese Examined Patent Application, Second Publication No.143-63430, Patent Reference 4: U.S. Pat. No. 4,559,314, Patent Reference 5: U.S. Pat. No. 4,784,747, Patent Reference 6: Japanese Patent, No. 2908959, Non Patent Reference 1: J. Catal., 93, 471 (1985), Non Patent Reference 2: J. Chem. Soc. Faraday Trans. 1, 81, 2215 (1985)).

However, the method for regenerating the dealuminated zeolite included a disadvantage in the applicability to industrial processes because of requirements for specific reagents or gas for the regeneration.

In addition, although the above-described method to compound the high-silica zeolite with alumina and to treat the compounded material with steam was examined on the zeolite containing a small amount of aluminum, for example a zeolite having a molar ratio of Si/Al>1200. The method was not examined on the zeolite having a molar ratio of Si/Al from several tens to ca. 300, which was frequently used in industrial processes.

On the other hand, it is known that the formation rate of carbonaceous deposits on the zeolite catalyst can be decreased by a proper steam treatment. In a disclosed method, catalytic lifetime for synthesizing hydrocarbons from methanol is increased by exposing MFI-structure zeolite catalyst to steam thereby controlling acid sites (active sites) of the zeolite (e.g., Patent Reference 7: U.S. Pat. No. 4,429,176, Patent Reference 8: U.S. Pat. No. 4,663,942, Patent Reference 9: U.S. Pat. No. 4,579,993). In addition, it is found that lifetime of an alumina-containing zeolite catalyst is prolonged by exposing the alumina-containing zeolite catalyst to steam thereby decreasing the coking rate of the catalyst (e.g., Patent Reference 10: U.S. Pat. No. 4,456,780). However, it has been unknown how the addition of alumina change the steam resistance of zeolite catalysts. In addition, there is no report treating a catalyst containing zeolite, alumina, and alkaline-earth metal compound with steam.

In DTO reaction/MTO reaction, it is disclosed that by using a proton-type MFI-structure zeolite impregnated with alkaline-earth metal compound, selectivity to lower olefins is increased, formations of paraffins and aromatic hydrocarbons are depressed, and formation of carbonaceous deposits is depressed, thereby prolonging lifetime of the catalyst (e.g., Patent Reference 11: Japanese Unexamined Patent Application, First Publication, No. S60-126233). However, in Patent Reference 11, it was not examined if lifetime of the zeolite catalyst modified with alkaline-earth metal compound was changed (or is not changed) by repeating regeneration of the catalyst after performing DTO reaction/MTO reaction In addition, steam resistance of the catalyst is not described in Patent Reference 11.

As a representative example of catalyst used for DTO reaction/MTO reaction, MFI-structure zeolite catalysts and SAPO-34 catalysts may be used.

In the DTO reaction/MTO reaction, activity of the catalyst is decreased by formation of carbonaceous deposits on the catalyst. Therefore, it is necessary to periodically introduce an oxygen-containing flow to the catalyst so as to burn the carbonaceous deposits on the catalyst, thereby regenerating the catalytic activity.

The combustion reaction to burn the carbonaceous deposits on the catalyst is an exothermal reaction. So as to prevent changing the catalyst such as collapse of crystal structure, and for a stable operation of apparatus used in the process, it is preferable to inhibit large increase of temperature. Therefore, in the above-described combustion reaction, so as to depress oxygen concentration to a lower level, the air introduced to the catalyst must be diluted by inert gas such as steam and nitrogen.

However, steam promote the elimination of aluminum from the zeolite catalyst to lead decreasing catalyst lifetime. Therefore, there is a method for using nitrogen as the dilution gas to keep the steam concentration at low level (e.g., U.S. Published Patent Application No, 2005/0085375)

It is difficult to apply the above-described method of regenerating dealuminated zeolite in industrial processes. In addition, the method includes a problem that an extra step is needed for inserting aluminum into the dealuminated zeolite. Therefore, in order to improve the lifetime of zeolite catalyst, it is necessary to produce a zeolite catalyst in which the framework aluminum is not likely to be eliminated.

On the other hand, when nitrogen gas is used to dilute the oxygen concentration in the regeneration atmosphere, a cryogenic air separator for producing the nitrogen gas is required, thereby increasing construction cost of a plant.

Based on the above described consideration, an object of the present invention is to provide an alkaline-earth metal compound-containing zeolite catalyst, in which the elimination of tetrahedral aluminum from the zeolite framework is not likely to occur, and a simple inexpensive method for preparing the above-described zeolite catalyst. Another object of the present invention is to provide a method for regenerating alkaline-earth metal compound-containing zeolite catalyst, by which method, catalytic activity of the alkaline-earth metal compound-containing zeolite catalyst is regenerated through a simple process, and lifetime of the catalyst is improved.

SUMMARY OF THE INVENTION

An alkaline-earth metal compound-containing zeolite catalyst according to the present invention is composed of a composite material comprising at least a first component, a second component, and a third component, wherein the first component is composed of at least one of zeolites selected from a group consisting of proton-type zeolites and ammonium type zeolites, the second component is composed of at least one of alkaline-earth metal compounds, and the third component is composed of at least one selected from a group consisting of aluminum oxides, aluminum hydroxides, silicon oxides, silicon hydroxides, and clay minerals. The first component has a molar ratio of Si/Al of 10 or more and 300 or less. Content of the second component relative to the first component is 0.3 mass % or more and less than 10 mass % as alkaline-earth metal. Content of the third component relative to the first component is 15 mass % or more and 200 mass % or less.

It is preferable that the alkaline-earth metal compound-containing zeolite catalyst according to the present invention comprises the above-described first component composed of at least one of MFI-structure zeolites.

It is preferable that the second component of the alkaline-earth metal compound-containing zeolite catalyst according to the present invention is composed at least one of calcium compounds.

An alkaline-earth metal compound-containing zeolite catalyst according to the present invention may has a characteristic such that where an alkaline-earth metal compound-containing zeolite catalyst according to the present invention is exposed for 48 hours to an atmosphere having steam partial pressure of 0.35 MPa and nitrogen partial pressure of 0.15 MPa at 530° C., and the residual amount of tetrahedral aluminum in zeolite framework per unit mass of zeolite is measured, the residual amount of tetrahedral aluminum in the zeolite catalyst of the present invention is not smaller than five times of the residual amount of tetrahedral aluminum in the proton-type zeolite consisting of the first component which has been exposed for 48 hours to the above described atmosphere.

An alkaline-earth metal compound-containing zeolite catalyst according to the present invention may be used for synthesizing lower hydrocarbons from DME and/or methanol, A method for preparing an alkaline-earth metal compound-containing zeolite catalyst according to the present invention comprises: a mixing-kneading step of adding polar solvent to a composition composed at least of a first component, a second component, and a third component, and kneading to form a mixture; and a drying-calcination step of drying and calcining the mixture, where the first component is composed of at least one of zeolites selected from a group consisting of proton-type zeolites and ammonium type zeolites, the second component is composed of at least one of alkaline-earth metal compounds, and the third component is composed of at least one selected from a group consisting of aluminum oxides, aluminum hydroxides, silicon oxides, silicon hydroxides, and clay minerals. The first component has a molar ratio of Si/Al of 10 or more and 300 or less. Content of the second component relative to the first component is 0.3 mass % or more and less than 10 mass % as alkaline-earth metal. Content of the third component relative to the first component is 15 mass % or more and 200 mass % or less.

It is preferable that a method for preparing an alkaline-earth metal compound-containing zeolite catalyst according to the present invention further comprises a steam treatment step where the composite material obtained by the above-described drying-calcination step is made contact to steam or reaction atmosphere that generates steam.

In a method for preparing an alkaline-earth metal compound-containing zeolite catalyst according to the present invention, the above-described first component is preferably composed of at least one of MFI-structure zeolites.

In a method for preparing an alkaline-earth metal compound-containing zeolite catalyst according to the present invention, it is preferable that the second component is composed of at least one of calcium compounds.

A method of producing lower hydrocarbons according to the present invention is a method for synthesizing lower hydrocarbons from DME and/or methanol, where the alkaline-earth metal compound-containing zeolite catalyst is used in the synthesis, and yield of propylene is 40 mass % or more, yield of methane is less than 1.0 mass %, and yield of carbon monoxide is 0.5 mass % or less.

A method for regenerating alkaline-earth metal compound-containing zeolite catalyst according to the invention is a method for regenerating alkaline-earth metal compound-containing zeolite catalyst used for synthesizing lower hydrocarbons from DME and/or methanol. The method includes a step of calcining an alkaline-earth metal compound-containing zeolite catalyst of the present invention in a flow containing oxygen and steam.

It is preferable that the above-described calcination of the alkaline-earth metal compound-containing zeolite catalyst is performed at 400° C. or more and 700° C. or less.

Effect of the Invention

An alkaline-earth metal compound-containing zeolite catalyst according to the present invention is composed of a composite material comprising at least a first component, a second component, and a third component, wherein the first component is composed of at least one of zeolites selected from a group consisting of proton-type zeolites and ammonium type zeolites, the second component is composed of at least one of alkaline-earth metal compounds, and the third component is composed of at least one selected from a group consisting of aluminum oxides, aluminum hydroxides, silicon oxides, silicon hydroxides, and clay minerals. The first component has a molar ratio of Si/Al of 10 or more and 300 or less, content of the second component relative to the first component is 0.3 mass % or more and less than 10 mass % as alkaline-earth metal, and content of the third component relative to the first component is 15 mass % or more and 200 mass % or less. The catalyst of this constitution has a long catalytic lifetime since the elimination of aluminum from the zeolite framework is inhibited by the presence of the second component and the third component. Therefore, by the improvement of overall catalytic lifetime, loading weight of catalyst and frequency of recharging the catalyst are reduced, and it is possible to reduce the equipment cost and the operation cost.

A method for preparing an alkaline-earth metal compound-containing zeolite catalyst according to the present invention comprises: a mixing-kneading step of adding polar solvent to a composition composed at least of a first component, a second component, and a third component, and kneading to form a mixture; and a drying-calcination step of drying and calcining the mixture, where the first component is composed of at least one of zeolites selected from a group consisting of proton-type zeolites and ammonium type zeolites, the second component is composed of at least one of alkaline-earth metal compounds, and the third component is composed of at least one selected from a group consisting of aluminum oxides, aluminum hydroxides, silicon oxides, silicon hydroxides, and clay minerals, the first component has a molar ratio of Si/Al of 10 or more and 300 or less, content of the second component relative to the first component is 0.3 mass % or more and less than 10 mass % as alkaline-earth metal, and content of the third component relative to the first component is 15 mass % or more and 200 mass % or less.

In this preparation method, an alkaline-earth metal compound-containing zeolite catalyst can be obtained easily and at low cost by using generally available and inexpensive proton-type MFF-structure zeolite or ammonium type MFI-structure zeolite, mixing with the second component and the third component, kneading, drying, and calcining the mixture of the zeolite. This catalyst is not likely to occur elimination of tetrahedral aluminum from the zeolite framework, and has excellent steam resistance and a long catalytic lifetime.

Since the alkaline-earth metal compound-containing zeolite catalyst is used in the method of producing lower hydrocarbons according to the present invention, lower hydrocarbons can be obtained at a high yield. In addition, by the improvement of the catalytic lifetime, frequency of regeneration is decreased. Therefore, productivity of lower hydrocarbons is increased and production cost can be reduced.

A method for regenerating alkaline-earth metal compound-containing zeolite catalyst according to the present invention is a method for regenerating alkaline-earth metal compound-containing zeolite catalyst used for synthesizing lower hydrocarbons from DME and/or methanol. In this method, the alkaline-earth metal compound-containing zeolite catalyst of the present invention is calcined in a flow containing oxygen and steam, thereby improving the catalytic lifetime. Therefore, frequency of regeneration of catalyst is decreased. As a result, it is possible to reduce the cost for synthesizing lower hydrocarbons from DME and/or methanol. In addition, since steam can be used as a dilution gas in the time of regenerating the catalyst, it is not necessary to provide extra facilities such as a cryogenic air separator or the like.

BRIEF EXPLANATION FOR DRAWINGS

FIG. 1 is a graph showing relative catalytic lifetime of catalysts A to F prepared in Experimental Examples 1-7 versus extent of steam treatment.

DETAILED DESCRIPTION OF THE INVENTION

BEST MODE FOR CARRYING OUT THE INVENTION

First Embodiment

An embodiment of an alkaline-earth metal compound-containing zeolite catalyst according to the present invention, a preparation method for same, and a method for producing lower hydrocarbons utilizing the alkaline-earth metal compound-containing zeolite catalyst is explained below.

It should be understood that this embodiment is an example to provide better understanding of the scope of the invention and the present invention is not limited to the description of this embodiment.

[Alkaline-Earth Metal Compound-Containing Zeolite Catalyst]

An alkaline-earth metal compound-containing zeolite catalyst according to the present invention is composed of a composite material comprising at least a first component, a second component, and a third component, wherein the first component is composed of at least one of zeolites selected from a group consisting of proton-type zeolites and ammonium type zeolites, the second component is composed of at least one of alkaline-earth metal compounds, and the third component is composed of at least one selected from a group consisting of aluminum oxides, aluminum hydroxides, silicon oxides, silicon hydroxides, and clay minerals. The first component has a molar ratio of Si/Al of 10 or more and 300 or less. Content of the second component relative to the first component is 0.3 mass % or more and less than 10 mass % as alkaline-earth metal. Content of the third component relative to the first component is 15 mass % or more and 200 mass % or less.

It is preferable that the alkaline-earth metal compound-containing zeolite catalyst according to the present invention comprises the above-described first component composed of at least one of MFI-structure zeolites, where "MFI-structure" is a name of a framework structure defined in the International Zeolite Association.

In the alkaline-earth metal compound-containing zeolite catalyst of the present invention, the proton-type zeolite or ammonium-type zeolite that constitutes the first component has a molar ratio of Si/Al of 10 or more and 300 or less.

Where the molar ratio of Si/Al is less than 10, too many acid sites exist on the catalyst surface and formation of carbonaceous deposits on the catalyst is enhanced, thereby shortening catalytic lifetime. On the other hand, if the molar ratio of Si/Al exceeds 300, effective acid sites are decreased thereby reducing catalytic activity.

It is preferable that the content of the second component as alkaline-earth metal relative to the first component be 0.3 mass % or more and less than 10 mass %

Where the content of the second component as alkaline-earth metal relative to the first component is less than 0.3 mass %, acidic properties of the catalyst and dealumination cannot be controlled sufficiently. On the other hand, where the content of the second component as alkaline-earth metal relative to the first component is more than 10 mass %, it is not preferable because side reactions are caused by excessive amount of the alkaline-earth metal compound (mainly composed of oxide and carbonate).

The content of the third component relative to the content of the first component is preferably 15 mass % or more and 200 mass % or less.

Where the content of the third component relative to the first component is less than 15 mass %, there occurs problems such as decrease in physical strength of the obtained catalyst resulting in powderization of the catalyst during using the catalyst. On the other hand, where the content of the third component relative to the first component exceeds 200 mass %, proportion of the first component active to the reaction is decreased, and catalytic performance is deteriorated.

In the alkaline-earth metal compound-containing zeolite catalyst of the present invention, it is preferable that the first component constituting the composite material is composed of at least one of zeolites selected from a group consisting of proton-type zeolites and ammonium type zeolites that have a MFI-structure. By using generally available and inexpensive proton-type zeolite or ammonium-type zeolite, it is possible to easily prepare an alkaline-earth metal-containing catalyst at low cost according to the present invention that has excellent steam resistance.

The alkaline-earth metal compound of the second component may be selected from magnesium carbonate ($MgCO_3$), magnesium hydroxide ($Mg(OH)_2$), magnesium oxide (MgO), magnesium acetate (($CH_3COO)_2Mg$), magnesium nitrate ($Mg(NO_3)_2$), magnesium aluminate ($MgAl_2O_4$), magnesium orthosilicate ($Mg_2SiO_4$), calcium carbonate ($CaCO_3$), calcium hydroxide ($Ca(OH)_2$), calcium oxide (CaO), calcium acetate (($CH_3COO)_2Ca$), calcium nitrate ($Ca(NO_3)_2$), calcium aluminate ($CaAl_2O_4$), calcium orthosilicate ($Ca_2SiO_4$), strontium carbonate ($SrCO_3$), strontium hydroxide ($Sr(OH)_2$), strontium oxide (SrO), strontium acetate (($CH_3COO)_2Sr$), strontium nitrate ($Sr(NO_3)_2$), strontium aluminate ($SrAl_2O_4$), strontium silicate, barium carbonate ($BaCO_3$), barium hydroxide ($Ba(OH)_2$), barium oxide (BaO), barium acetate (($CH_3COO)_2Ba$), barium nitrate ($Ba(NO_3)_2$), barium aluminate ($BaAl_2O_4$), barium silicate or the like.

The third component is composed of at least one selected from a group consisting of aluminum oxides, aluminum hydroxides, silicon oxides, silicon hydroxides, and clay minerals.

For example, γ-alumina ($Al_2O_3$) or the like may be applied as the aluminum oxides.

As the aluminum hydroxides, boehmite (AlO(OH)), aluminum hydroxide ($Al(OH)_3$), alumina sol or the like may be used.

Silicon dioxide ($SiO_2$) may be used as the silicon oxides.

Silicon hydroxides may have a form of orthosilicate ($H_4SiO_4$), metasilicate ($H_2SiO_3$) or the like.

Kaolin, bentonite or the like may be used as the clay minerals.

Where necessary, additives composed of graphite, cellulose or the like may be added to the alkaline-earth metal compound-containing zeolite catalyst of the present invention.

Where an alkaline-earth metal compound-containing zeolite catalyst of the above-described constitution is exposed for 48 hours to an atmosphere having steam partial pressure of 0.35 MPa and nitrogen partial pressure of 0.15MPa at 530° C., and a proton-type zeolite consisting only of the above-described first component is exposed to the same atmosphere under the same condition, after the exposure, the residual amount of tetrahedral aluminum in the zeolite framework per unit mass of zeolite in the alkaline-earth metal compound-containing catalyst is preferably not smaller than 5 times, more preferably not smaller than 10 times, of the residual amount of tetrahedral aluminum in the zeolite framework per unit mass of zeolite in the proton-type zeolite consisting of the first component.

Where the residual amount of tetrahedral aluminum in the zeolite framework per unit mass of zeolite in the alkaline-earth metal compound-containing catalyst after exposure to the above-described conditions is not smaller than 5 times of the residual amount of tetrahedral aluminum in the zeolite framework per unit mass of zeolite in the proton-type zeolite consisting of the first component treated with steam under the same condition, it is possible to reduce the degree of deterioration of catalytic activity caused by exposure to steam in the reaction atmosphere or in the regeneration atmosphere. Therefore, it is possible to increase the number of times of regeneration of the catalyst, and decrease the frequency for recharging the catalyst.

An alkaline-earth metal compound-containing zeolite catalyst according to the present invention is composed of a composite material comprising at least a first component, a second component, and a third component, wherein the first component is composed of at least one of zeolites selected from a group consisting of proton-type zeolites and ammonium type zeolites, the second component is composed of at least one of alkaline-earth metal compounds, and the third component is composed of at least one selected from a group consisting of aluminum oxides, aluminum hydroxides, silicon oxides, silicon hydroxides, and clay minerals, where the first component has a molar ratio of Si/Al of 10 or more and 300 or less, content of the second component relative to the first component is 0.3 mass % or more and less than 10 mass % as alkaline-earth metal, and content of the third component relative to the first component is 15 mass % or more and 200 mass % or less. Since both the second component and the third component inhibit the elimination of aluminum from zeolite framework, the zeolite catalyst of the above-described constitution has a long catalytic lifetime. Therefore, by the improvement of the overall catalytic lifetime, loading weight of catalyst and frequency of recharging the catalyst are reduced, and it is possible to reduce the equipment cost and the operation cost of the reaction system.

[Method of Preparing the Alkaline-Earth Metal Compound-Containing Zeolite Catalyst]

A method of preparing an alkaline-earth metal compound-containing zeolite catalyst of the present invention is explained below.

Mixing-Kneading Step

Firstly, by using mortar, milling machine, kneader or the like, a composition at least containing a first component, a second component, and a third component is mixed with a polar solution and kneaded, to prepare a mixture composed of at least the first component, the second component, the third component, and polar solution.

In this mixing-kneading step, at least one of zeolites having a Si/Al molar ratio of 10 or more and 300 or less, selected from a group consisting of proton-type zeolites and ammonium type zeolites is used as the first component.

At least one of alkaline-earth metal compounds is used as the second component.

As the third component, at least one selected from a group consisting of aluminum oxides, aluminum hydroxides, silicon oxides, silicon hydroxides, and clay minerals is used.

In the mixing-kneading step, content of the second component relative to the first component is controlled to be 0.3 mass % or more and less than 10 mass %.

Content of the third component relative to the first component is controlled to be 15 mass % or more and 200 mass % or less.

In addition, relative to the amount of the composition at least containing the first component, the second component, and the third component, added amount of polar solution is controlled to be 10 mass % or more and 150 mass % or less.

As the polar solution, water is most preferably used. In addition, it is possible to use organic polar solution including alcohol group solution such as ethanol and propanol, ether group solution such as diethyl ether and tetrahydrofuran, ester group solution, amid group solution, sulfoxide group solution.

In addition, in the time of producing a composite material, in addition to the polar solution, it is also possible to add a material which is to be removed in the time of drying and calcining. Such material may include organic acid such as acetic acid, aqueous ammonia, graphite, cellulose group or the like.

Molding Step

Next, the mixture obtained in the mixing-kneading step is formed into a shaped catalyst, for example, by extrusion molding using an extruder, or by spheronization molding using a spheronizer (marumerizer).

Drying-Calcination Step

Next, the shaped catalyst obtained in the molding step is dried by a drying machine, and is subjected to calcination using a furnace such as muffle furnace, tunnel furnace or the like, thereby preparing a composite material. Thus, the alkaline-earth metal compound-containing zeolite catalyst according to the invention can be obtained.

In the above-described drying-calcination step, it is preferable to perform the drying of the shaped catalyst under conditions at 80° C. or more and 150° C. or less for a duration of 0.5 hours or more and 30 hours or less.

In the drying-calcination step, it is preferable that the shaped catalyst after drying is subjected to calcination at 350° C. or more and 750° C. or less for a duration of not shorter than 1 hour and not longer than 50 hours, A method for preparing an alkaline-earth metal compound-containing zeolite catalyst according to the present invention comprises: mixing-kneading step of adding polar solvent to a composition composed at least of a first component, a second component, and a third component, and kneading to form a mixture; and drying-calcination step of drying and calcining the mixture to prepare a composite material, where the first component is composed of at least one of zeolites selected from a group consisting of proton-type zeolites and ammonium type zeolites, the second component is composed of at least one of alkaline-earth metal compounds, and the third component is composed of at least one selected from a group consisting of aluminum oxides, aluminum hydroxides, silicon oxides, silicon hydroxides, and clay minerals. The first component has a molar ratio of Si/Al of 10 or more and 300 or less, content of the second component relative to the first component defined is 0.3 mass % or more and less than 10 mass % as alkaline-earth metal, and content of the third component relative to the first component is 15 mass % or more and 200 mass % or less.

In this preparation method, by constituting the first component using generally available proton-type zeolite and/or ammonium-type zeolite, and by mixing and kneading the first component with the second component and the third component to form a mixture, and drying and calcining the mixture, it is possible to produce simply and inexpensively an alkaline-earth metal compound-containing zeolite catalyst having excellent steam resistance, and long catalytic lifetime.

[Method of Producing Lower Hydrocarbons]

In the following, a method of producing lower hydrocarbons from DMB and/or methanol is described as an embodiment utilizing the alkaline-earth metal compound-containing zeolite catalyst of the present invention.

Steam Treatment Step

The alkaline-earth metal compound-containing zeolite catalyst consisting of the composite material obtained in the above-described drying-calcination step may be subjected to a steam treatment step where the catalyst is made contact to steam; or air and/or inert gas (e.g., nitrogen and carbon dioxide) that contains steam in an amount of not less than 10 vol %. Alternatively, the catalyst may be made contact to reaction atmosphere that generates steam. In the steam treatment, it is allowable to use conditions in which steam partially exist as liquid water. In addition, it is possible to perform the steam treatment step simultaneously with the drying-calcination step.

The above described reaction that generates steam refers to the reaction in which dehydration of reactants occurs on the catalyst surface, thereby generating steam. DTO reaction/MTO reaction and dehydration of alcohol are examples of the reaction.

In the steam treatment step, it is preferable that the duration for making the composite material contact to steam or the reaction atmosphere generating steam is not shorter than 1 hour and not longer than 50 hours.

So as to synthesize lower hydrocarbons from one or both of DME and methanol utilizing the alkaline-earth metal compound-containing zeolite catalyst treated with steam, DME and/or methanol is supplied as a gas, and the gas is made contact with the alkaline-earth metal compound-containing zeolite catalyst. As the method for making the catalyst to contact with the gas, fixed bed reactor or fluid bed reactor may be applied.

In the method of producing lower hydrocarbons, the synthetic reaction of lower hydrocarbons from DME and/or methanol may be performed using a wide range of temperature/pressure conditions.

Preferably, the reaction temperature is not lower than 300° C. and not higher than 750° C., more preferably not lower than 400° C. and not higher than 650° C. Where the reaction temperature is lower than 300° C., activity of the catalyst is not sufficient. Where the reaction temperature exceeds 750° C., formation rate of the carbonaceous deposits is fast, catalytic activity is reduced rapidly, and change of the catalyst such as collapse of the zeolite structure Occurs.

In the method of producing lower hydrocarbons, DME and/or methanol as a raw material may be diluted with steam, inert gas, carbon dioxide or the like and is supplied to the alkaline-earth metal compound-containing zeolite catalyst.

Especially, when lower hydrocarbons are synthesized continuously using a fixed-bed reactor, the weight hourly space velocity (WHSV), which is the ratio of the supplied quantity of DME as a raw material to the quantity of the catalyst, is preferably not less than 0.025 g-DME/(g-catalyst·hour) and not more than 50 g-DME/(g-catalyst·hour).

Where the WHSV is less than 0.025 g-DME/(g-catalyst·hour), it is not cost effective since space time yield is reduced. On the other hand, where the WHSV is higher than 50 g-DME/(g-catalyst·hour), catalytic lifetime and catalytic activity are not sufficient.

The lower hydrocarbons generated on the alkaline-earth metal compound-containing zeolite catalyst flow out from the reactor, and can be separated to objective products in accordance with generally-known separation-purification method.

In the method for producing lower hydrocarbons, by using the alkaline-earth metal compound-containing zeolite catalyst of the present invention, it is possible to synthesize lower hydrocarbons from DME and/or methanol at a high yield.

Second Embodiment

An embodiment of a method of regenerating an alkaline-earth metal compound-containing zeolite catalyst of the present invention is explained in the following.

It should be understood that this embodiment is an example for providing better understanding of the scope of the present invention and the present invention is not limited to the description of this embodiment.

A method of regenerating alkaline-earth metal compound containing zeolite catalyst according to the present invention is a method for regenerating alkaline-earth metal compound containing zeolite catalyst used for synthesizing lower hydrocarbons from DME and/or methanol. The method includes a step of calcining an alkaline-earth metal compound-containing zeolite catalyst of the present invention in a flow containing oxygen and steam.

In the method of regenerating an alkaline-earth metal compound-containing zeolite catalyst according to the present invention, after performing synthesis of lower hydrocarbons from one or both of DME and methanol for a certain period of time utilizing the alkaline-earth metal compound-containing zeolite catalyst, the alkaline-earth metal compound-containing zeolite catalyst is calcined in a flow that contains oxygen and steam, thereby regenerating catalytic activity.

In the method of regenerating an alkaline-earth metal compound-containing zeolite catalyst according to the present invention, proportion of the flow rate of steam relative to the flow rate of oxygen in the flow containing oxygen and steam is preferably not less than 5 and not more than 2000, more preferably, not less than 15 and not more than 1000.

Where the proportion of the flow rate of steam relative to the flow rate of oxygen is less than 5, oxygen is not diluted sufficiently, and temperature of catalyst bed is increased by combustion heat caused by burning carbonaceous deposits on the catalyst, thereby causing a possible change of the catalyst, such as collapse of the structure. In addition, it is possible that an effect of steam treatment cannot be obtained sufficiently. On the other hand, where the proportion of the flow rate of steam relative to the flow rate of oxygen exceeds 2000, because of too low oxygen concentration, burning the carbonaceous deposits on the catalyst occurs slowly, and long time is required for regenerating the catalyst.

In the method of regenerating an alkaline-earth metal compound-containing zeolite catalyst according to the present invention, the flow containing oxygen and steam may contain a recycled exhaust gas from the reactor being used for regenerating the catalyst, and inert gas such as carbon dioxide and argon gas.

In the method of regenerating an alkaline-earth metal compound-containing zeolite catalyst according to the present invention, it is preferable that a temperature for calcining the alkaline-earth metal compound-containing zeolite catalyst is preferably not lower than 400° C. and not higher than 700° C., more preferably, not lower than 450° C. and not higher than 650° C.

Where the temperature for calcining the alkaline-earth metal compound-containing zeolite catalyst is less than 400° C., carbonaceous deposits on the catalysts cannot be burned, and catalytic activity cannot be recovered sufficiently. On the other hand, where the temperature for calcining the alkaline-earth metal compound-containing zeolite catalyst exceeds 700° C., change of the catalyst such as collapse of zeolite structure may occur.

The period for calcining the alkaline-earth metal compound-containing zeolite catalyst at the above-described temperature range is preferably not shorter than 3 hours and not longer than 300 hours, more preferably, not shorter than 5 hours and not longer than 150 hours.

Where the period for calcining the alkaline-earth metal compound-containing zeolite catalyst is shorter than 3 hours, carbonaceous deposits on the catalyst cannot be burned sufficiently, and catalytic activity cannot be recovered sufficiently. On the other hand, where the period for calcining the alkaline-earth metal compound containing zeolite catalyst exceeds 300 hours, since the catalyst is exposed to the flow containing oxygen and steam for a long time, dealumination of the zeolite proceeds resulting in reduction of catalytic lifetime.

A method of regenerating alkaline-earth metal compound containing zeolite catalyst according to the invention is a method for regenerating alkaline-earth metal compound containing zeolite catalyst used for synthesizing lower hydrocarbons from DME and/or methanol. In this method, by calcining the alkaline-earth metal compound-containing zeolite catalyst in a flow that contains oxygen and steam, it is possible to improve the lifetime of the catalyst. Therefore, frequency of regenerating the catalyst is reduced, resulting in reduction of cost for synthesizing lower hydrocarbons from DME and/or methanol. In addition, in the time of regenerating the catalyst, steam may be used as a dilution gas. Therefore, requirement for extra facilities such as a cryogenic air separator for nitrogen production can be avoided.

EXAMPLE

Example of the First Embodiment

The present invention is explained in detail based on the following examples. However, it should be understood that the present invention is not limited to the following examples.

Preparation of Zeolite Catalyst

Experimental Example 1

100 g of an ammonium type MFI-structure zeolite (CBV150140 provided by Zeolyst International) having a molar ratio of Si/Al of 75 was calcined at 550° C. and proton-type MFI-structure zeolite was obtained. Hereafter, this catalyst is referred to as catalyst A.

Experimental Example 2

The catalyst A in an amount of 100 g was mixed with 5.0 g of calcium carbonate ($CaCO_3$) under solid state and a mixture of both materials was prepared. The mixture was calcined at 550° C. for 6 hours in air. The thus obtained catalyst is hereafter referred to as catalyst B.

Experimental Example 3

100 g of the above-described ammonium type MFI structure zeloite was mixed with 5.0 g of calcium carbonate. After adding an appropriate amount of ion-exchanged water, the mixture was kneaded and a mixed body was prepared. After drying the mixed body at 120° C., the mixed body was calcined at 550° C. for 12 hours in air. The thus obtained catalyst is hereafter referred to as catalyst C.

Experimental Example 4

100 g of the above-described ammonium type MFI structure zeloite was mixed with 28 g of boehmite (containing 70% of $Al_2O_3$). After adding an appropriate amount of ion-exchanged water, the mixture was kneaded and a mixed body was prepared. The mixed body was extruded using an extruder. A shaped catalyst obtained by the extrusion molding was dried at 120° C., and was calcined at 550° C. for 12 hours in the air. The thus obtained catalyst is hereafter referred to as catalyst D.

Experimental Example 5

100 g of the above-described ammonium type MFI structure zeolite was mixed with 28 g of the above-described boehmite and 5.0 g of calcium carbonate. After adding an appropriate amount of ion-exchanged water, the mixture was kneaded and a mixed body was prepared. The mixed body was extruded using an extruder. A shaped catalyst obtained by the extrusion molding was dried at 120° C., and was calcined at 550° C. for 12 hours in the air. The thus obtained catalyst is hereafter referred to as catalyst E.

Experimental Example 6

100 g of the above-described ammonium type MFI structure zeloite was mixed with 28 g of the above-described boehmite and 25 g of calcium carbonate. After adding an appropriate amount of ion-exchanged water, the mixture was kneaded and a mixed body was prepared. The mixed body was extruded using an extruder. A shaped catalyst obtained by the extrusion molding was dried at 120° C., and was calcined at 550° C. for 12 hours in the air. Thus obtained catalyst is hereafter referred to as catalyst F.

Experimental Example 7

100 g of the above-described ammonium type MFI structure zeloite was mixed with 262 g of the above-described boehmite and 5.0 g of calcium carbonate. After adding an appropriate amount of ion-exchanged water, the mixture was kneaded and a mixed body was prepared. The mixed body was extruded using an extruder. A shaped catalyst obtained by the extrusion molding was dried at 120° C., and was calcined at 550° C. for 12 hours in the air. Thus obtained catalyst is hereafter referred to as catalyst G.

Evaluation of Steam Resistance of Catalysts

Comparative Example A1

In order to evaluate the steam resistance, the catalyst A obtained by the Experimental Example 1 was subjected to the following treatment.

The catalyst A was evacuated at 400° C. for 3 hours. After that, $^{27}$Al-MAS-NMR spectrum of the catalyst A was measured using a NMR spectrometer (Bruker DRX-400), thereby performing quantitative analysis of the amount of tetrahedral aluminum in zeolite framework per unit mass of zeolite. The measured amount of tetrahedral aluminum in zeolite framework in Comparative Example A1 was defined as 100.

Comparative Example A2

The catalyst A was subjected to a steam treatment by exposing the catalyst to an atmosphere having steam partial pressure of 0.35 MPa, nitrogen partial pressure of 0.15 MPa, at 530° C., for 48 hours.

The catalyst A treated with steam was evacuated at 400° C. for 3 hours. After that, $^{27}$Al-MAS-NMR spectrum of the catalyst A treated with steam was measured using an NMR spectrometer (Bruker DRX-400), thereby performing quantitative analysis of the amount of tetrahedral aluminum in zeolite framework per unit mass of zeolite. The relative amount of the tetrahedral aluminum in the Comparative Example A2 compared to the amount of tetrahedral aluminum in the Comparative Example A1 is shown in Table 1.

Comparative Example A3

The catalyst B obtained by the Experimental Example 2 was subjected to the same treatments as the Comparative Example A1, and in the same manner as described-above, relative amount of the tetrahedral aluminum in the Comparative Example A3 compared to the amount of tetrahedral aluminum in the Comparative Example A1 was determined. The result is shown in Table 1.

Comparative Example A4

The catalyst B was subjected to the same treatments as the Comparative Example A2, and in the same manner as described-above, the relative amount of the tetrahedral aluminum in the Comparative Example A4 compared to the amount of tetrahedral aluminum in the Comparative Example A1 was determined. The result is shown in Table 1.

Comparative Example A5

The catalyst C obtained by the Experimental Example 3 was subjected to the same treatments as the Comparative Example A1, and in the same manner as described-above, the relative amount of the tetrahedral aluminum in the Comparative Example A5 compared to the amount of tetrahedral aluminum in the Comparative Example A1 was determined. The result is shown in Table 1.

Comparative Example A6

The catalyst C was subjected to the same treatments as the Comparative Example A2, and in the same manner as described-above, the relative amount of the tetrahedral aluminum in the Comparative Example A6 compared to the amount of tetrahedral aluminum in the Comparative Example A1 was determined. The result is shown in Table 1.

Comparative Example A7

The catalyst D obtained by the Experimental Example 4 was subjected to the same treatments as the Comparative Example A1, and in the same manner as described-above, the relative amount of the tetrahedral aluminum in the Comparative Example A7 compared to the amount of tetrahedral aluminum in the Comparative Example A1 was determined, The result is shown in Table 1.

Comparative Example A8

The catalyst D was subjected to the same treatments as the Comparative Example A2, and in the same manner as described-above, the relative amount of the tetrahedral aluminum in the Comparative Example A8 compared to the amount of tetrahedral aluminum in the Comparative Example A1 was determined. The result is shown in Table 1.

Comparative Example A9

The catalyst F obtained by the Experimental Example 6 was subjected to the same treatments as the Comparative Example A1, and in the same manner as described-above, the relative amount of the tetrahedral aluminum in the Comparative Example A9 compared to the amount of tetrahedral aluminum in the Comparative Example A1 was determined. The result is shown in Table 1.

Comparative Example A10

The catalyst F was subjected to the same treatments as the Comparative Example A2, and in the same manner as described-above, the relative amount of the tetrahedral aluminum in the Comparative Example A10 compared to the amount of tetrahedral aluminum in the Comparative Example A1 was determined. The result is shown in Table 1.

Example A1

The catalyst E obtained by the Experimental Example 5 was subjected to the same treatments as the Comparative Example A1, and in the same manner as described-above, the relative amount of the tetrahedral aluminum in the Example A1 compared to the amount of tetrahedral aluminum in the Comparative Example A1 was determined. The result is shown in Table 1.

Example A2

The catalyst E was subjected to the same treatments as the Comparative Example A2, and in the same manner as described-above, relative amount of the tetrahedral aluminum in the Example A2 compared to the amount of tetrahedral aluminum in the Comparative Example A1 was determined. The result is shown in Table 1.

TABLE 1

| | Relative amount of tetrahedral aluminum (%) |
|---|---|
| Comparative Example A1 | 100 |
| Comparative Example A2 | 6 |
| Comparative Example A3 | 104 |
| Comparative Example A4 | 22 |
| Comparative Example A5 | 100 |
| Comparative Example A6 | 29 |
| Comparative Example A7 | 115 |
| Comparative Example A8 | 36 |
| Comparative Example A9 | 155 |
| Comparative Example A10 | 63 |
| Example A1 | 142 |
| Example A2 | 86 |

Tetrahedral aluminum in the zeolite framework cause acid sites, that is catalytic active sites. Where a catalyst is exposed to steam atmosphere, the tetrahedral aluminum are eliminated from the framework to lead a decrease of acid sites and the catalytic activity. Therefore, the catalyst having a large amount of residual tetrahedral aluminum after the exposure to steam atmosphere can be regarded as a catalyst having high steam resistance, and not likely to subject the elimination of tetrahedral aluminum from the zeolite framework.

With respect to Comparative Examples A1 and A2, it was confirmed that the amount of tetrahedral aluminum in the catalyst A decreased to 6% after exposing the catalyst to an atmosphere having steam partial pressure of 0.35 MPa, nitrogen partial pressure of 0.15 MPa, at 530° C., for 48 hours, With respect to Comparative Examples A3 and A4, it was confirmed that the relative amount of tetrahedral aluminum in the catalyst B decreased to 22% after exposing the catalyst to an atmosphere having steam partial pressure of 0.35 MPa, nitrogen partial pressure of 0.15 MPa, at 530° C., for 48 hours.

It is considered that calcium carbonate added to the catalyst B inhibited the elimination of tetrahedral aluminum from the zeolite framework.

With respect to Comparative Examples A5 and A6, it was confirmed that the relative amount of tetrahedral aluminum in the catalyst C decreased to 29% after exposing the catalyst to an atmosphere having steam partial pressure of 0.35 MPa, nitrogen partial pressure of 0.15 MPa, at 530° C., for 48 hours.

The catalyst C was prepared by kneading MFI zeolite and calcium carbonate in the presence of water, and calcining the mixture. Therefore, compared to catalyst B in which raw materials were mixed in a solid state, it is considered that calcium carbonate were highly dispersed into the micropore of the zeolite and it would be more effective to prevent the elimination of tetrahedral aluminum from the zeolite framework.

In Comparative Example A7, catalyst D showed the relative amount of tetrahedral aluminum of 115%, which was increased compared to that in the catalyst A. It is considered that because of the addition of boehmite, aluminum atoms are inserted into the zeolite framework during the calcination.

In Comparative Example A8, it was confirmed that the amount of tetrahedral aluminum in the catalyst D decreased to 36% after exposing the catalyst to an atmosphere having steam partial pressure of 0.35 MPa, nitrogen partial pressure of 0.15 MPa, at 530° C., for 48 hours. The elimination of tetrahedral aluminum from Catalyst D was suppressed compared with that in Catalyst A. Aluminum oxide and/or aluminum hydroxide species would exist in the zeolite catalyst after calcining the zeolite and boehmite mixture. The aluminum oxide and/or aluminum hydroxide species may inhibit the elimination of tetrahedral aluminum.

In Comparative Example A9, catalyst F showed a relative amount of tetrahedral aluminum of 155%, which was more than the catalyst A. The addition of boehmite may cause the insertion of aluminum into the zeolite framework during calcination.

In Comparative Example A10, it was confirmed that the amount of tetrahedral aluminum in the catalyst F decreased to 63% after exposing the catalyst to an atmosphere having steam partial pressure of 0.35 MPa, nitrogen partial pressure of 0.15 MPa, at 530° C., for 48 hours. In Comparative A10, it was confirmed that by adding boehmite and calcium carbonate to the zeolite, it was possible to obtain a catalyst which was not likely to subject elimination of tetrahedral aluminum and had high steam resistance.

In Example A1, catalyst E showed a relative amount of tetrahedral aluminum of 142%. It was confirmed that the residual amount of tetrahedral aluminum in the catalyst E was increased compared to the catalyst A. It is considered that because of the addition of boehmite, aluminum are inserted into the zeolite framework during the calcination.

In Example A2, it was confirmed that the amount of tetrahedral aluminum in the zeolite framework decreased to 86% after exposing the catalyst to an atmosphere having steam partial pressure of 0.35 MPa, nitrogen partial pressure of 0.15 MPa, at 530° C., for 48 hours. In Example A2, composing the MFI zeolite with the appropriate amount of aluminum oxide and/or aluminum hydroxide and calcium carbonate, can yield the most steam rersistant catalyst which has the least possibility of the elimination of tetrahedral aluminum from the zeolite framework among all catalysts in Table 1.

Test of Catalytic Performance

In order to test the catalytic performance of catalysts A to G obtained in Experimental Examples 1 to 7, lower hydrocarbons were synthesized from DME utilizing the catalysts A to G. Here, catalytic lifetime was defined as an elapsed time from the time the reaction started to the time the conversion of DME became less than 99.0%. Yields (mass %) of propylene, methane, and yield of carbon monoxide were analyzed by gas chromatograph at 10-15 hours after the beginning of the reaction. The yield of each product was based on the weight of carbon atoms contained in the supplied DME and/or methanol.

Comparative Example A11

Performance of the catalyst A was tested with an isothermal reactor. DME and nitrogen were mixed together at flow rates of 1,272 Ncm$^3$/hour and 1,272 Ncm$^3$/hour, respectively. Then, the resulting mixture was transferred to an isothermal reactor, and reacted with the catalyst A at 530° C. under atmospheric pressure. The weight hourly space velocity (WHSV), which is the ratio of the supplied quantity of DME as a raw material to the quantity of the catalyst, was set to be 9.6 g-DME/(g-catalyst·hour). Relative catalytic lifetime, and yields (in mass %) of propylene, methane and carbon monoxide are shown in Table 2. The relative catalytic lifetime denotes a lifetime compared to the catalytic lifetime in Comparative Example A11 which was defined as 100.

Comparative Example A12

Catalyst A was treated with steam for 24 hours by exposing the catalyst to an atmosphere having steam partial pressure of 0.08 MPa, nitrogen partial pressure of 0.02 MPa, at 530° C. Performance of the steam-treated catalyst A was tested with an isothermal reactor. DME and nitrogen were mixed together at flow rates of 1,272 Ncm$^3$/hour and 1,272 Ncm$^3$/hour, respectively. Then, the resulting mixture was transferred to an isothermal reactor, and reacted with the steam-treated catalyst A at 530° C. under atmospheric pressure. The weight hourly space velocity (WHSV), which is the ratio of the supplied quantity of DME as a raw material to the quantity of the catalyst, was set to be 9.6 g-DME/(g-catalyst·hour). Relative catalytic lifetime, and yields (in mass %) of propylene, methane and carbon monoxide are shown in Table 2.

Comparative Example A13

Catalyst A was treated with steam for 48 hours by exposing the catalyst to an atmosphere having steam partial pressure of 0.35 MPa, nitrogen partial pressure of 0.15 MPa, at 530° C. Performance of the steam-treated catalyst A was tested with an isothermal reactor. DME and nitrogen were mixed together at flow rates of 1,272 Ncm$^3$/hour and 1,272 Ncm$^3$/hour, respectively. Then, the resulting mixture was transferred to an isothermal reactor, and reacted with the steam-treated catalyst A at 530° C. under atmospheric pressure. The weight hourly space velocity (WHSV), which is the ratio of the supplied quantity of DME as a raw material to the quantity of the catalyst, was set to be 9.6 g-DME/(g-catalyst·hour). Relative catalytic lifetime, and yields (in mass %) of propylene, methane and carbon monoxide are shown in Table 2.

Comparative Example A14

Catalyst A was treated with steam for 96 hours by exposing the catalyst to an atmosphere having steam partial pressure of 0.35 MPa, nitrogen partial pressure of 0.15 MPa, at 530° C. Performance of the steam-treated catalyst A was tested with an isothermal reactor. DME and nitrogen were mixed together at flow rates of 1,272 Ncm$^3$/hour and 1,272 Ncm$^3$/hour, respectively. Then, the resulting mixture was transferred to an isothermal reactor, and reacted with the steam-treated catalyst A at 530° C. under atmospheric pressure. The weight hourly space velocity (WHSV), which is the ratio of the supplied quantity of DME as a raw material to the quantity of the catalyst, was set to be 9.6 g-DME/(g-catalyst~hour), The relative catalytic lifetime, and yields (in mass %) of propylene, methane and carbon monoxide are shown in Table 2.

Comparative Example A15

Performance of the Catalyst B was tested in the same manner as in Comparative Example A11. The relative catalytic lifetime, and yields (in mass %) of propylene, methane and carbon monoxide are shown in Table 2.

Comparative Example A16

Performance of the Catalyst B was tested in the same manner as in Comparative Example A12, The relative catalytic lifetime, and yields (in mass %) of propylene, methane and carbon monoxide are shown in Table 2.

Comparative Example A17

Performance of the Catalyst B was tested in the same manner as in Comparative Example A13. The relative catalytic lifetime, and yields (in mass %) of propylene, methane and carbon monoxide are shown in Table 2.

Comparative Example A18

Performance of the Catalyst C was tested in the same manner as in Comparative Example A11. The relative catalytic lifetime, and yields (in mass %) of propylene, methane and carbon monoxide are shown in Table 2.

Comparative Example A19

Performance of the Catalyst C was tested in the same manner as in Comparative Example A12. The relative catalytic lifetime, and yields (in mass %) of propylene, methane and carbon monoxide are shown in Table 2.

Comparative Example A20

Performance of the Catalyst C was tested in the same manner as in Comparative Example A13. The relative catalytic lifetime, and yields (in mass %) of propylene, methane and carbon monoxide are shown in Table 2.

Comparative Example A21

Performance of the Catalyst C was tested in the same manner as in Comparative Example A14. The relative catalytic lifetime, and yields (in mass %) of propylene, methane and carbon monoxide are shown in Table 2.

Comparative Example A22

Performance of the Catalyst D was tested in the same manner as in Comparative Example A11. The relative catalytic lifetime, and yields (in mass %) of propylene, methane and carbon monoxide are shown in Table 2.

Comparative Example A23

Performance of the Catalyst D was tested in the same manner as in Comparative Example A12. The relative catalytic lifetime, and yields (in mass %) of propylene, methane and carbon monoxide are shown in Table 2.

Comparative Example A24

Performance of the Catalyst D was tested in the same manner as in Comparative Example A13, The relative catalytic lifetime, and yields (in mass %) of propylene, methane and carbon monoxide are shown in Table 2.

Comparative Example A25

Performance of the Catalyst D was tested in the same manner as in Comparative Example A14. The relative catalytic lifetime, and yields (in mass %) of propylene, methane and carbon monoxide are shown in Table 2.

Comparative Example A26

Performance of the Catalyst F was tested in the same manner as in Comparative Example A1 1. The relative catalytic lifetime, and yields (in mass %) of propylene, methane and carbon monoxide are shown in Table 2.

Comparative Example A27

Performance of the Catalyst F was tested in the same manner as in Comparative Example A13. The relative catalytic lifetime, and yields (in mass %) of propylene, methane and carbon monoxide are shown in Table 2.

Example A3

Performance of the Catalyst E was tested in the same manner as in Comparative Example A11, The relative catalytic lifetime, and yields (in mass %) of propylene, methane and carbon monoxide are shown in Table 2.

Example A4

Performance of the Catalyst E was tested in the same manner as in Comparative Example Al2, The relative catalytic lifetime, and yields (in mass %) of propylene, methane and carbon monoxide are shown in Table 2.

Example A5

Performance of the Catalyst E was tested in the same manner as in Comparative Example A13, The relative catalytic lifetime, and yields (in mass %) of propylene, methane and carbon monoxide are shown in Table 2.

Example A6

Performance of the Catalyst E was tested in the same manner as in Comparative Example A14. The relative catalytic lifetime, and yields (in mass %) of propylene, methane and carbon monoxide are shown in Table 2.

Example A7

Performance of the Catalyst G was tested in the same manner as in Comparative Example A12. The relative catalytic lifetime, and yields (in mass %) of propylene, methane and carbon monoxide are shown in Table 2.

TABLE 2

|  | Relative lifetime | Yield of propylene (mass %) | Yield of methane (mass %) | Yield of CO (mass %) |
| --- | --- | --- | --- | --- |
| Comparative Example A11 | 100 | 34 | 3.3 | 0.35 |
| Comparative Example A12 | 346 | 42 | 1.9 | 0.20 |
| Comparative Example A13 | 0 | 32 | 1,1 | 0.05 |
| Comparative Example A14 | 0 | 15 | 1.1 | 0.03 |
| Comparative Example A15 | 142 | 43 | 1.8 | 0.80 |
| Comparative Example A16 | 546 | 42 | 0.9 | 0.60 |
| Comparative Example A17 | 371 | 42 | 0.8 | 0.65 |
| Comparative Example A18 | 268 | 42 | 1.7 | 0.22 |
| Comparative Example A19 | 478 | 44 | 0.7 | 0.13 |
| Comparative Example A20 | 927 | 44 | 0.6 | 0.00 |
| Comparative Example A21 | 0 | 38 | 1.1 | 0.15 |
| Comparative Example A22 | 99 | 32 | 6.0 | 0.50 |
| Comparative Example A23 | 591 | 42 | 0.9 | 0.25 |
| Comparative Example A24 | 544 | 44 | 0.8 | 0.06 |
| Comparative Example A25 | 0 | 36 | 0.7 | 0.08 |
| Comparative Example A26 | 693 | 39 | 1.8 | 3.10 |
| Comparative Example A27 | 1033 | 46 | 1.0 | 1.56 |
| Example A3 | 306 | 42 | 1.5 | 0.83 |
| Example A4 | 440 | 42 | 0.8 | 0.07 |
| Example A5 | 900 | 46 | 0.7 | 0.07 |
| Example A6 | 514 | 42 | 0.7 | 0.00 |
| Example A7 | 221 | 40 | 0.9 | 0.10 |

FIG. 1 shows the relative lifetime of catalysts versus the extent of steam treatments, In FIG. 1, the horizontal axis denotes the extent of steam treatment which was defined by the product of steam partial pressure and the duration of the steam treatment. The vertical axis of FIG. 1 denotes the relative catalytic lifetime of catalysts A-G in Comparative Examples A11-A27 and Examples A3-A7 compared to the lifetime of catalyst A in Comparative Example A11 which was defined as 100.

From the results shown in Table 2 and FIG. 1, it was confirmed that catalytic lifetimes of catalysts A to E were improved by treating the catalysts with steam under mild condition by exposing to an atmosphere having steam partial pressure of 0.08 MPa, nitrogen partial pressure of 0.02 MPa, at 530° C., for 24 hours (Comparative Examples A11, A12, A15, A16, A18, A19, A22, A23, Examples A3, A4). This improvement can be explained by moderate reduction of acid sites (active sites) in zeolite caused by elimination of the tetrahedral aluminum. In catalyst D and catalyst E, steaming can also reduce the acid sites on alumina, which contribute undesirable side reactions, and improve the catalytic lifetime.

After the steam treatment for exposing a catalyst for 48 hours to an atmosphere having steam partial pressure of 0.35 MPa, nitrogen partial pressure of 0.15 MPa, at 530° C., catalytic lifetime of the catalyst A was reduced to 0, and catalytic lifetimes of catalyst B and catalyst D were decreased. On the other hand, catalytic lifetimes of catalyst C and catalyst E were further improved (Comparative Example A13, A17, A20, A24, Example A5).

After the steam treatment for exposing a catalyst for 96 hours to an atmosphere having steam partial pressure of 0.35 MPa, nitrogen partial pressure of 0.15 MPa, at 530° C., catalytic lifetimes of catalyst C and catalyst D were reduced to 0, and catalytic lifetime of catalyst E was decreased (Comparative Example A21, A25, Example A6).

The above-described trend can be explained by the elimination of the tetrahedral aluminum from the zeolite framework accompanied by the steam treatment, that is, reduction of acid sites (active sites). Where catalysts A to E are treated with steam for relatively short duration, the moderate reduction of acid sites depress the formation of carbonaceous deposits, thereby increasing catalytic lifetime. On the other hand, where the catalysts are further treated with steam for relatively long duration, acid sites are decreased to too low level, thereby leaking DME in early stage and reducing catalytic lifetime. A catalyst that exhibits long catalytic lifetime even after the severe steam treatment is not likely to subject elimination of tetrahedral aluminum from the zeolite framework and has high steam resistance.

From the result of FIG. 1, steam resistance of catalysts A to E can be expressed as catalyst E>catalyst C>catalyst D>catalyst B>catalyst A. This order approximately corresponds with the order of residual proportion of tetrahedral aluminum obtained by $^{27}$Al-MAS-NMR spectra (Table 1).

Catalyst F had long catalytic lifetime even when the steam treatment was not performed (Comparative Example A26), It is considered that a large content of calcium carbonate contribute the improvement of the catalytic lifetime. After treating the catalyst F with steam by exposing to an atmosphere having steam partial pressure of 0.35 MPa, nitrogen partial pressure of 0.15 MPa, at 530° C., for 48 hours, catalytic lifetime of the catalyst F was increased and showed a long catalytic lifetime comparable to catalyst C and catalyst E (Comparative Example 27).

By the use of catalysts A, C, D, and E that were not treated with steam, methane of not less than 1.0 mass % and/or carbon monoxide of not less than 0.3 mass % were generated (Comparative Examples A11, A18, A22, and Example A3). Even after the catalyst A treated with steam, yield of methane was not less than 1.0 mass % (Comparative Examples A12 to A14). When catalysts C, D, E were treated with steam to an appropriate degree such that each catalyst did not lose its activity, yield of methane was less than 1.0 mass %, and yield of carbon monoxide was less than 0.3 mass % (Comparative Examples A19, A20, A23, A24, and Examples A4 to A6).

When catalyst B was used without the steam treatment, yield of methane was 1.8 mass %, and yield of carbon monoxide was 0.80 mass % (Comparative Example A15). When catalyst B was used after the steam treatment, yield of methane was 0.8 to 0.9 mass % and yield of carbon monoxide was 0.60 to 0.65 mass %. Therefore, it was confirmed that even when the catalyst B was treated with steam, these side reactions could not be inhibited sufficiently (Comparative Examples A16, A17).

When catalyst F was used without the steam treatment, yield of methane was 1.8 mass %, and yield of carbon monoxide was 3.10 mass % which was higher than the case of using the other catalysts (Comparative Example A26). It was considered that high calcium content in catalyst F resulted in the decomposition of DME on the basic sites.

When catalyst F was used after the steam treatment, yield of methane was 1.0 mass % and yield of carbon monoxide was 1.56 mass %. Therefore, it was confirmed that even when the catalyst F was treated with steam, these side reactions could not be inhibited sufficiently (Comparative Examples A27).

By using catalyst G, yield of propylene was 40 mass %, yield of methane was 0.9 mass %, and yield of carbon monoxide was 0.10 mass % (Example A7).

Based on the above-described results, the catalyst E, which was obtained by mixing ammonium type MFI structure zeolite with boehmite and appropriate amount of calcium carbonate, kneading the mixture with appropriate amount of ion-exchanged water, drying and calcining the mixture, had the highest steam resistance. In addition, by treating the catalyst E with steam, catalytic lifetime was largely enhanced and side reactions such as generation of methane and generation of carbon monoxide could be effectively inhibited.

The catalyst F, which was obtained by mixing ammonium type MFI structure zeolite with boehmite and a large amount of calcium carbonate, kneading the mixture with appropriate amount of ion-exchanged water, drying and calcining the mixture, had relatively high steam resistance. However, even after the steam treatment, side reactions such as generation of methane and generation of carbon monoxide could not be inhibited by the use of the catalyst F. Even though recycled in a reactor, methane and carbon monoxide have poor reactivity and are not converted to olefin. Therefore decomposition reaction for generating methane and carbon monoxide is not desirable. It is understood that the catalyst F is not appropriately used for a reaction for generating lower hydrocarbons from DME and/or methanol.

From the results of evaluation of steam resistance of the catalysts and catalytic performance tests, the following can be proposed.

In catalyst C, which was obtained by mixing ammonium type MFI-structure zeolite with appropriate amount of calcium carbonate, kneading the mixture with ion-exchanged water, drying and calcining the mixture, elimination of tetrahedral aluminum from the zeolite framework was inhibited by the calcium compound, resulting in higher steam resistance than that of catalyst A consisting of proton type MFI-structure zeolite.

In catalyst D, which was obtained by mixing ammonium type MFI-structure zeolite with boehmite, kneading the mixture with ion-exchanged water, drying and calcining the mixture, elimination of aluminum from the zeolite framework was inhibited by the effect of aluminum oxide and/or aluminum hydroxide, resulting in higher steam resistance than that of catalyst A consisting of proton type MFI-structure zeolite.

The catalyst E, which was obtained by mixing ammonium type MFI structure zeolite with boehmite and appropriate amount of calcium carbonate, kneading the mixture with ion-exchanged water, drying and calcining the mixture, had the highest steam resistance by the effects of calcium compound and aluminum oxide and/or aluminum hydroxide.

When the catalyst E was used in the reaction without steam treatment, yields of methane and carbon monoxide were relatively high and catalytic lifetime was not so long. By treating catalyst E with steam, side reactions were inhibited and catalytic lifetime was largely enhanced.

The catalyst F, which was obtained by mixing ammonium type MFI structure zeolite with boehmite and a large amount of calcium carbonate, kneading the mixture with ion-exchanged water, drying and calcining the mixture, had lower steam resistance than that of catalyst E (Table 1). In addition, in the reaction using the catalyst F, methane and carbon monoxide showed high yields. Even after treating catalyst F with steam, methane and carbon monoxide showed high yields in the reaction using catalyst F.

Example of the Second Embodiment

Preparation of Zeolite Catalysts

Zeolite catalysts D and E were prepared in the same manners as above-described Experimental Examples 4 and 5, respectively.

Experimental Example 8

In accordance with the method of preparing a zeolite catalyst disclosed in a Patent Reference (Japanese Unexamined Patent Application, First Publication No. 2005-138000), Ca-containing MFI-structure zeolite catalyst was obtained. This catalyst is hereafter referred to as catalyst H.

Test of Catalytic Performance

In order to test catalytic performance of catalysts D, E, and H obtained in Experimental Examples 4, 5, and 8, lower hydrocarbons were synthesized from DME utilizing the catalysts D, E, and H.

Here, catalytic lifetime was defined as an elapsed time from the time the reaction started to the time the conversion of DME became less than 99.0%.

Comparative Example B1

Catalyst D was treated with steam for 24 hours by exposing the catalyst to an atmosphere having a steam partial pressure of 0.08 MPa, nitrogen partial pressure of 0.02 MPa, at 530° C.

Performance of the steam-treated catalyst D was tested with an isothermal reactor. DME and nitrogen were mixed together at flow rates of 1,272 Ncm$^3$/hour and 1,272 Ncm$^3$/hour, respectively. Then, the resulting mixture was transferred to an isothermal reactor, and reacted with the steam-treated catalyst D at 530° C. under atmospheric pressure. The weight hourly space velocity (WHSV), which is the ratio of the supplied quantity of DME as a raw material to the quantity of the catalyst, was set to be 9.6 g-DME/(g-catalyst·hour). DME and nitrogen were supplied to the reactor until the DME conversion was decreased to 5% or less.

Comparative Example B2

Air and nitrogen were mixed together at flow rates of 143Ncm$^3$/hour and 1,272 Ncm$^3$/hour, respectively. Then, the resulting mixture was transferred to the isothermal reactor, thereby burning carbonaceous deposits on the catalyst D used in Comparative Example B1 at 550° C. under atmospheric pressure. After that, catalytic performance was tested in the same manner as in Comparative Example B1. Relative catalytic lifetime of Comparative Example B2 compared to the catalytic lifetime of Comparative Example B1 defined as 100 was shown in Table 3.

Example B1

Catalyst D was treated with steam for 24 hours by exposing the catalyst to an atmosphere having a steam partial pressure of 0.08 MPa, nitrogen partial pressure of 0.02 MPa, at 530° C.

Using the steam-treated catalyst D, catalytic performance was tested in the same manner as in Comparative Example B1.

Example B2

Air and steam were mixed together at flow rates of 143Ncm$^3$/hour and 1,272 Ncm$^3$/hour, respectively. Then, the resulting mixture was transferred to the isothermal reactor, thereby burning carbonaceous deposits on the catalyst D used in Example B1 at 550° C. under atmospheric pressure. After that, catalytic performance was tested in the same manner as in Comparative Example B1. Relative catalytic lifetime of Example B2 compared to the catalytic lifetime of Example B1 defined as 100 was shown in Table 3.

Comparative Example B3

Catalyst E was treated with steam for 24 hours by exposing the catalyst to an atmosphere having a steam partial pressure of 0.08 MPa, nitrogen partial pressure of 0.02 MPa, at 530° C.

Using the steam-treated catalyst E, catalytic performance was tested in the same manner as in Comparative Example B1.

Comparative Example B4

Air and nitrogen were mixed together at flow rates of 143Ncm$^3$/hour and 1,272 Ncm$^3$/hour, respectively. Then, the resulting mixture was transferred to the isothermal reactor, thereby burning carbonaceous deposits on the catalyst E used in Comparative Example B3 at 550° C. under atmospheric pressure. After that, catalytic performance was tested in the same manner as in Comparative Example B1. Relative catalytic lifetime of Comparative Example B4 compared to the catalytic lifetime of Comparative Example B3 defined as 100 was shown in Table 3.

Example B3

Catalyst E was treated with steam for 24 hours by exposing the catalyst to an atmosphere having a steam partial pressure of 0.08 MPa, nitrogen partial pressure of 0.02 MPa, at 530° C.

Using the steam-treated catalyst E, catalytic performance was treated in the same manner as in Comparative Example B1.

Example B4

Air and steam were mixed together at flow rates of 143Ncm$^3$/hour and 1,272 Ncm$^3$/hour, respectively. Then, the resulting mixture was transferred to the isothermal reactor, thereby burning carbonaceous deposits on the catalyst E used in Example B3 at 550° C. under atmospheric pressure. After that, in the same manner as in Comparative Example B1, test of catalytic performance was performed in an isothermal reactor. Relative catalytic lifetime of Example B4 compared to the catalytic lifetime of Example B3 defined as 100 was shown in Table 3.

Comparative Example B5

Catalyst H was treated with steam for 24 hours by exposing the catalyst to an atmosphere having a steam partial pressure of 0.08 MPa, nitrogen partial pressure of 0.02 MPa, at 530° C.

Using the steam-treated catalyst catalytic performance was tested in the same manner as in Comparative Example B1.

Comparative Example B6

Air of and nitrogen were mixed together at flow rates of 143Ncm$^3$/hour and 1,272 Ncm$^3$/hour, respectively. Then, the resulting mixture was transferred to the isothermal reactor, thereby burning carbonaceous deposits on the catalyst H used in Comparative Example B5 at 550° C. under atmospheric pressure. After that, catalytic performance was tested in the same manner as in Comparative Example B1. Relative catalytic lifetime of Comparative Example B6 compared to the catalytic lifetime of Comparative Example B5 defined as 100 was shown in Table 3.

Comparative Example B7

Catalyst H was treated with steam for 24 hours by exposing the catalyst to an atmosphere having a steam partial pressure of 0.08 MPa, nitrogen partial pressure of 0.02 MPa, at 530° C.

Using the steam-treated catalyst H, catalytic performance was tested in the same manner as in Comparative Example B1.

Comparative Example B8

Air and steam were mixed together at flow rates of 143Ncm$^3$/hour and 1,272 Ncm$^3$/hour, respectively. Then, the resulting mixture was transferred to the isothermal reactor, thereby burning carbonaceous deposits on the catalyst H used in Comparative Example B7 at 550° C. under atmospheric pressure. After that, catalytic performance was tested in the same manner as in Comparative Example B1. Relative catalytic lifetime of Comparative Example B8 compared to the catalytic lifetime of Comparative Example B7 defined as 100 was shown in Table 3.

TABLE 3

|  | Relative lifetime |
| --- | --- |
| Comparative Example B1 | 100 |
| Comparative Example B2 | 89 |
| Example B1 | 100 |
| Example B2 | 110 |
| Comparative Example B3 | 100 |
| Comparative Example B4 | 74 |
| Example B3 | 100 |
| Example B4 | 113 |
| Comparative Example B5 | 100 |
| Comparative Example B6 | 101 |
| Comparative Example B7 | 100 |
| Comparative Example B8 | 98 |

From the results shown in Table 3, the followings were confirmed.

In Comparative Examples B1, B2, catalyst D was treated with steam and was used in a synthetic reaction of lower hydrocarbons from DME, and was subsequently regenerated in a flow of air and nitrogen. In this case, catalytic lifetime was decreased after the regeneration.

In Examples B1, B2, catalyst D was treated with steam and was used in a synthetic reaction of lower hydrocarbons from DME, and was subsequently regenerated in a flow of air and steam. In this case, catalytic lifetime was improved by the regeneration.

In Comparative Examples B3, B4, catalyst E was treated with steam and was used in a synthetic reaction of lower hydrocarbons from DME, and was subsequently s regenerated in a flow of air and nitrogen. In this case, catalytic lifetime was decreased after the regeneration.

In Examples B3, B4, catalyst E was treated with steam and was used in a synthetic reaction of lower hydrocarbons from DME, and was subsequently regenerated in a flow of air and steam. In this case, catalytic lifetime was improved by the regeneration.

In Comparative Examples B5, B6, catalyst H was treated with steam and was used in a synthetic reaction of lower hydrocarbons from DME, and was subsequently regenerated in a flow of air and nitrogen. In this case, catalytic lifetime was almost unchanged by the regeneration.

In Comparative Examples B7, B8, catalyst H was treated with steam and was used in a synthetic reaction of lower hydrocarbons from DME, and was subsequently regenerated in a flow of air and steam. In this case, catalytic lifetime was almost unchanged by the regeneration.

From the results described above, it is possible to derive the following interpretations.

With respect to the Catalyst D, which is composed of MFI-structure zeolite and aluminum oxide and/or aluminum hydroxide, and Catalyst E, which is composed of MFI-structure zeolite, calcium carbonate, and aluminum oxide and/or aluminum hydroxide, it is possible to improve the catalytic lifetime after the regeneration in a flow containing air and steam.

With respect to the Catalyst H, which is composed of Ca-containing MFI-structure zeolite without aluminum oxide nor aluminum hydroxide, catalytic lifetime did not largely change before and after the regeneration, whether steam was supplied or not during the regeneration.

From these observations, it is considered that regenerating the catalysts in the presence of steam and air is effective for the catalyst D, which is composed of MFI-structure zeolite and aluminum oxide and/or aluminum hydroxide, and the catalyst E, which is composed of MFI-structure zeolite, aluminum oxide and/or aluminum hydroxide, and calcium carbonate. It is considered that the steam may operate the nature of aluminum oxide and/or aluminum hydroxide to improve the catalytic lifetime.

INDUSTRIAL APPLICABILITY

An alkaline-earth metal compound-containing zeolite catalyst and method for preparing the same according to the present invention may be applied to various processes such as synthetic reaction of gasoline using methanol as the raw material (MTG reaction), olefin cracking, fluid catalytic cracking (FCC), hydrogen dewaxing, isomerization of paraffin, production of aromatic hydrocarbon, alkylation of aromatic compound, oxidation reaction using hydrogen peroxide, and production of ethanolamine group.

A method of regenerating an alkaline-earth metal compound containing zeolite catalyst according to the present invention may be applied to regeneration step of catalyst in various processes such as synthetic reaction of gasoline using methanol as the raw material (MTG reaction), cracking or the like.

The invention claimed is:
1. A method for preparing an alkaline-earth metal compound-containing zeolite catalyst, comprising:
   a mixing-kneading step of adding polar solvent to a composition composed at least of a first component, a second component, and a third component, and kneading to form a mixture;
   a drying-calcination step of drying and calcining the mixture to form a composite material; and
   a steam treatment step of contacting the composite material obtained by the drying-calcination step with steam or a reaction atmosphere that generates steam;
   wherein the first component is composed of at least one of MFI-structure zeolites selected from a group consisting of proton-type zeolites and ammonium type zeolites,
   the second component is composed of calcium carbonate, the third component is composed of at least one compound selected from a group consisting of aluminum oxides, aluminum hydroxides, silicon oxides, silicon hydroxides, and clay minerals, the first component has a molar ratio of Si/Al of 10 or more and 300 or less, the content of the second component relative to the first component is 0.3 mass % or more and less than 10 mass % as alkaline-earth metal, the content of the third component relative to the first component is 15 mass % or more and 200 mass % or less, and the extent of steam treatment in the steam treatment step is 1.92 to 16.8 in A.U., said extent of steam treatment being defined by the product of steam partial pressure in MPa and a duration of the steam treatment in hours.

2. The method for preparing an alkaline-earth metal compound-containing zeolite catalyst according to claim 1, wherein the amount of the polar solvent relative to the amount of a composition at least containing the first component, the second component, and the third component is 10 mass % or more and 150 mass % or less.

3. The method for preparing an alkaline-earth metal compound-containing zeolite catalyst according to claim 1, wherein drying in the drying-calcination step is performed at a temperature of 80° C. or more and 150° C. or less for a duration of 30 hours or less.

4. The method for preparing an alkaline-earth metal compound-containing zeolite catalyst according to claim 1, wherein calcination in the drying-calcination step is performed at a temperature of 350° C. or more and 750° C. or less for a duration of not longer than 50 hours.

* * * * *